United States Patent [19]
Vera et al.

[11] Patent Number: 5,549,710
[45] Date of Patent: Aug. 27, 1996

[54] SYSTEM FOR ASSEMBLING TWO COMPONENTS OF A PROSTHESIS IN A PLURALITY OF ADJUSTABLE POSITIONS

[75] Inventors: Bernard Vera, Seurre, France; Olivier Pierron, Luxembourg, Luxembourg

[73] Assignee: Etablissements Proteor, Dijon, France

[21] Appl. No.: 188,457

[22] Filed: Jan. 28, 1994

[30] Foreign Application Priority Data

Feb. 3, 1993 [FR] France ................................ 93 01156
Jul. 28, 1993 [FR] France ................................ 93 09297

[51] Int. Cl.⁶ .................................................. A61F 2/62
[52] U.S. Cl. ............................ 623/38; 623/27; 403/362; 403/375
[58] Field of Search .................................. 403/362, 375, 403/374, 381; 623/33, 38, 41, 43, 45, 48, 65

[56] References Cited

U.S. PATENT DOCUMENTS

| | | | |
|---|---|---|---|
| 272,315 | 2/1883 | Pease | 403/362 |
| 2,606,777 | 10/1949 | Wilson | 403/362 |
| 3,659,294 | 5/1972 | Glabiszewski | 623/38 |
| 4,007,496 | 2/1977 | Glabiszewski | 623/38 |
| 4,020,929 | 5/1977 | Goldin | 403/362 |
| 4,608,054 | 8/1986 | Schröder | 623/39 |
| 4,676,800 | 6/1987 | Chen | 623/38 |
| 4,923,472 | 5/1990 | Ugolini | 623/20 |
| 4,969,911 | 11/1990 | Greene | 623/38 |
| 5,013,325 | 5/1991 | Rennerfelt | 623/38 |
| 5,047,063 | 9/1991 | Chen | 623/38 |
| 5,070,662 | 12/1991 | Niese | 52/127.7 |

FOREIGN PATENT DOCUMENTS

| | | | |
|---|---|---|---|
| 0102853 | 3/1984 | European Pat. Off. . | |
| 0224373 | 6/1987 | European Pat. Off. . | |
| 1541573 | 3/1979 | United Kingdom | 403/362 |
| 2141345 | 12/1984 | United Kingdom . | |
| 2250562 | 6/1992 | United Kingdom | 403/381 |

*Primary Examiner*—David Isabella
*Assistant Examiner*—Laura Fossum
*Attorney, Agent, or Firm*—Scully, Scott, Murphy & Presser

[57] ABSTRACT

A system for assembling two components of a prosthesis in a plurality of positions which are adjustable in orthogonal translation, and selectively in rotation and angularly. In the system, a projecting part integral with one of these components is engaged in a recess, forming a hollow part of the other component of the prosthesis, or of an intermediate connection element, while screws arranged transversely with respect to the lateral walls of the cell come into abutment, as in the prior art, against the lateral flanks of the projecting part, but without the base of the hollow part bearing directly against the facing surface of the projecting part. Outer edges of the recess forming the hollow part bear in such a way against sets of screw so as to be able to slide in a rectilinear manner in at least one direction relative to the extent of a surface of the component with which the projecting part is integral, this projecting part being spaced in any position thereof from the base of the recess forming the hollow part.

3 Claims, 8 Drawing Sheets

SYSTEM FOR ASSEMBLING TWO COMPONENTS OF A PROSTHESIS IN A PLURALITY OF ADJUSTABLE POSITIONS

BACKGROUND OF THE INVENTION

1. Field of the Invention

The present invention relates to a system for assembling two components of a prosthesis in a plurality of adjustable positions.

It is known that the alignment and orientation of parts of a prosthesis must be carried out with care, and relatively complicated and expensive junction pieces are often used for this purpose.

It has already been proposed to use modular junction members which are intended to form part of a prosthesis of a limb of the human body and to join two components of this prosthesis to one another in an adjustable manner.

2. Discussion of the Prior Art

Thus, GB-A-2,141,345 describes an adjustable connection device for joining two parts of a prosthesis, this device comprising first and second connection elements which are each intended to be fixed on the parts of the prosthesis to be joined, the connection elements being in mutual contact or in contact with an intermediate connection member via flat or spherical parts bearing directly against one another and capable of being displaced with respect to one another by sliding or by pivoting, screws being provided for locking them in position after adjustment.

In one of the embodiments described in this prior document, a projecting member, integral with a part of the prosthesis, is housed in a recessed portion, in the form of a cellular or hollow part, of an intermediate connection member and bears via a flat part against the base of the part in the form of a hollow part, against which it can thus slide in order to be brought by translation from the desired position. Screws engaged in internal threads arranged transversely in the lateral walls of the hollow part can bear via a free end against the lateral flanks of the projecting member, which are inclined with respect to the base of the hollow part, with a view to locking this member in position.

On account of the direct contact between the base of the hollow part and the projecting part, very substantial moments are exerted on the latter, which thus risks breaking or cracking and which must consequently be made of a material capable of withstanding the stresses which are applied to it.

SUMMARY OF THE INVENTION

The present invention aims to overcome this disadvantage by providing a system for assembling two components of a prosthesis in a plurality of positions which are adjustable in translation, in rotation and angularly, in which system a projecting part integral with one of the these components is, as previously, engaged in a recess, forming a hollow part, of the other component of the prosthesis or of an intermediate connection element (or vice versa), while screws arranged transversely with respect to the lateral walls of the cell come into abutment, as in the prior art, against the lateral flanks of the projecting part, but without the base of the hollow part bearing directly against the facing surface of the projecting part, thereby preventing the latter from being subjected to very substantial stresses or moments.

To this end, in accordance with the present invention, the outer edge of the recess forming the hollow part bears in such a way as to be able to slide in a rectilinear manner in at least one direction on a surface of the component with which the projecting part is integral, this projecting part furthermore being spaced apart, in any position, from the base of the recess forming the hollow part.

When, in this definition of the invention, mention is made of a recess forming a hollow part, this is not of course intended to limit the invention to a precise form of hollow part. The same applies to the projecting part, which can have any form lending itself to a locking by screws coming into abutment against its lateral flanks.

In practice, it is therefore via the edges of the hollow part that the part in which this recess is formed bears, in such a way as to be able to slide, against a surface of an element integral with the base of the projecting part, and the stresses which will be exerted by the portion in which the hollow part is formed are not therefore transmitted to the projecting part, but are distributed in a ring around the latter onto the element which is integral therewith, thereby preventing risks of breakage or damage of the projecting part.

By means of relative sliding between the element integral with the base of the projecting part and the edges of the recess forming the hollow part, it will thus be possible to adjust in translation, as desired, the position of the two parts of a prosthesis, or of one part of a prosthesis and an intermediate connection element between this part and another part of the prosthesis.

It will be possible for the edge of the hollow part to bear via at least one first flat surface against at least one second flat surface of the element integral with the projecting part and, in such a form of implementation of the invention, by means of relative sliding of the first flat surface against the second flat surface, it will be possible to adjust in translation, in any direction, the position of the two parts of a prosthesis, or of one part of a prosthesis and an intermediate connection element.

It will also be possible for the edge of the hollow part to bear via at least one first cylindrical surface against at least one second cylindrical surface of complementary profile of the element with which the projecting part is integral, and in such an embodiment it will be possible for the first and second surfaces to slide with respect to one another in a direction parallel to the axis of the cylindrical surfaces and to pivot with respect to one another about the axis of the cylindrical surface, in order to permit the adjustment of their relative positions.

Finally, the various elements will advantageously be adjustable with respect to one another by rotation about an axis perpendicular to the flat sliding surfaces or to the axis of cylindrical sliding surfaces.

In the embodiments which will be described hereinbelow with reference to the attached drawings, the projecting parts will have the form of a truncated pyramid with a rectangular base, and they will project from a cylindrical part to which the projecting part will be connected via the small base of the truncated pyramid. These forms of implementation of the invention are preferred forms, by virtue of their simplicity, but they are of a non-limiting nature.

One embodiment of the invention thus consists of a modular connection device, which is adjustable in position, between two components of a prosthesis, this device comprising a first element capable of being made integral with a first component of the prosthesis, a second element capable of being made integral with a second component of the prosthesis, and an intermediate element capable of being made integral, in an adjustable position, with the first and second elements, respectively, by cooperation of a male part and/or a female part, respectively, of this intermediate element, with a female part and/or a male part of the first and the second elements, assembly members such as screws being provided for locking with respect to one another, in a plurality of positions, on the one hand the first element and the intermediate element, and on the other hand the second element and the intermediate element, this device being characterized in that each of the said male parts comprises a portion in the form of a truncated pyramid with a rectangular base projecting from a portion of cylindrical form, to which it is connected via its small base, the axis of the cylindrical portion being substantially parallel to two sides of the base of the associated truncated pyramid, while each female part comprises a portion of a form complementary to that of the cylindrical element and a recessed portion in the form of a groove capable of receiving the portion of the associated male element in the form of a truncated pyramid, the groove having dimensions greater than those of the portion in the form of a truncated pyramid, parallel to the axis of the cylindrical portion and perpendicular thereto, in such a way as to afford a double freedom of movement, in rotation with respect to this axis and in translation parallel to this axis, of the male portion with respect to the associated female portion, the cylindrical parts associated with each of the first and second elements furthermore having axes which are non-parallel and, preferably, perpendicular to each other.

By virtue of this connection device, it is thus possible, as indicated hereinabove, to pivot each of the male cylindrical portions with respect to the corresponding female portion and to displace each of the male portions in the form of a truncated pyramid in translation with respect to the groove of the associated female part in which it is housed, which thus affords two possibilities of angular adjustment of the components of the prosthesis with respect to one another, and two possibilities of adjustment in translation.

In the definition of the invention given hereinabove, the term cylindrical form encompasses all the surfaces allowing the female parts and the associated male parts to pivot with respect to one another about a common axis of rotation.

It will be possible for the intermediate element of the connection device to comprise two male parts each associated with a female part of the first and second elements of the device. Conversely, it will be possible for the intermediate element to comprise two female parts, each associated with a male part of the first and second elements of the connection device. Finally, as an alternative, it will be possible for the intermediate element to comprise a single male part associated with a female part of one of the first and second elements, and a single female part associated with a male part of one of the first and second elements of the device.

Screws, which are screwed into threaded recesses in the first and second elements of the device and come into abutment against the flanks of the portions in the form of a truncated pyramid, make it possible, after adjusting the relative positions of the components of the prosthesis which are integral, respectively, with the first and second elements of the device, to lock these elements in their respective positions.

BRIEF DESCRIPTION OF THE DRAWINGS

The invention will be described hereinbelow in greater detail, with reference to the attached diagrammatic drawings in which.

DETAILED DESCRIPTION OF PREFERRED EMBODIMENTS

Figure 1:
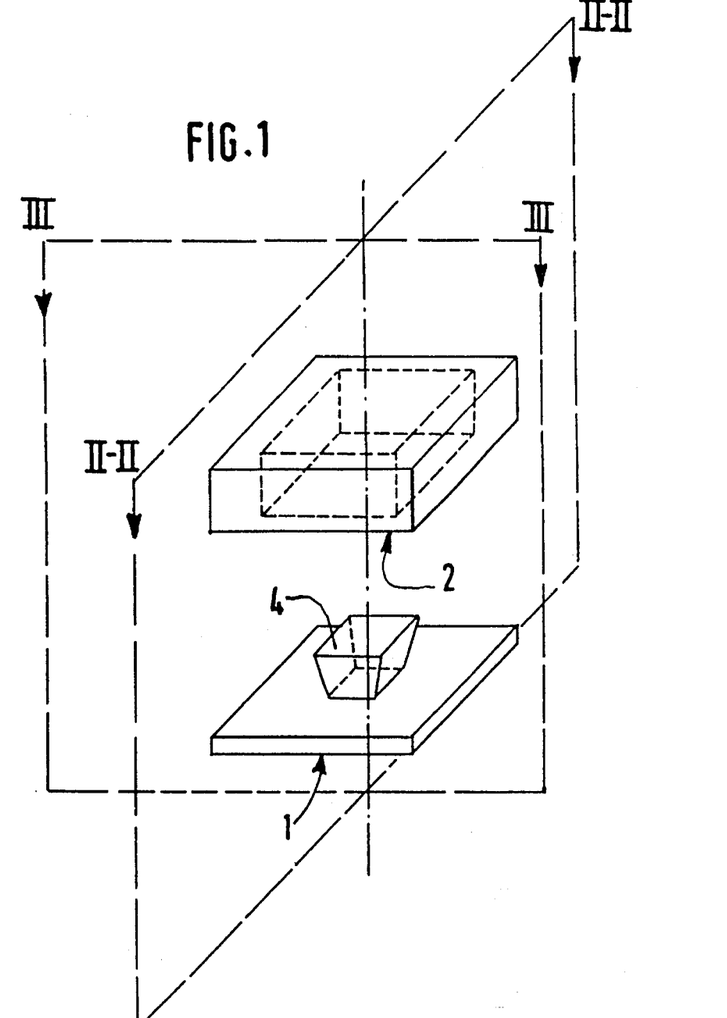
FIG. 1 is a perspective partial view of two parts of a prosthesis or of one part of a prosthesis and a part of an intermediate connection element, in mutual contact via coplanar surfaces.

It will be seen that the system according to the invention comprises two pieces 1 and 2 which can each be joined to a part of a prosthesis or of a connection element between two parts of a prosthesis, but which can also form an integral part of this prosthesis part or this connection part.

The piece 1 comprises a flat plate 3, from the surface of which there projects a part 4 which here has the form of an inverted truncated pyramid, that is to say a truncated pyramid whose larger base is remote from the plate 3, but which could have any other form. In the case of the drawing, the piece 1 is represented as being monobloc, but the plate 3 and the part 4 could just as well be separate and be made integral with one another by any means known in the art.

Figure 2:
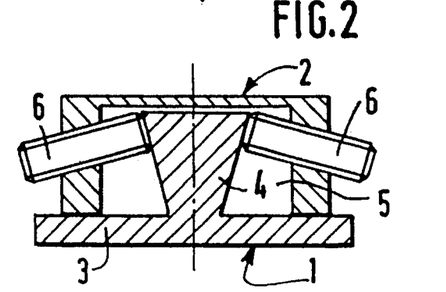
FIGS. 2 and 3 are sections along the lines II—II and III—III in FIG. 1, respectively.
Figure 3:
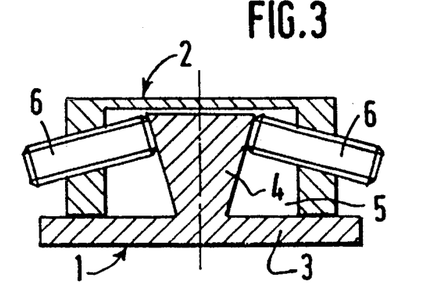

The piece 2 can have any form. It comprises a recess forming a hollow cell 5, the edges of which rest via a flat part against the surface of the plate 3 from which the part 4 projects. The latter is engaged in the recess 5 forming the hollow cell, but without coming into contact with the base thereof, in contrast to the systems of the prior art.

In a manner known per se, screws engaged in threaded transverse recesses in the lateral walls of the hollow cell 5 can come into abutment against the inclined flanks of the part 4 in order to immobilize the latter in position and, consequently, to lock the part 1 with respect to the part 2.

When the screws 6 are not holding the pieces 1 and 2 in the assembled state, it is possible to slide these pieces against one another in any direction in order to adjust their relative position in translation.

Since the piece 2 does not bear against the projecting part 4, the latter is not subjected to any stress and does not risk breaking, cracking or being damaged, as in the prior art. In contrast, the stresses of the part 2 are exerted against the surface of the plate 3, all around the part 4, and are thus distributed over this entire surface, which withstands them without any problem.

Figure 4:
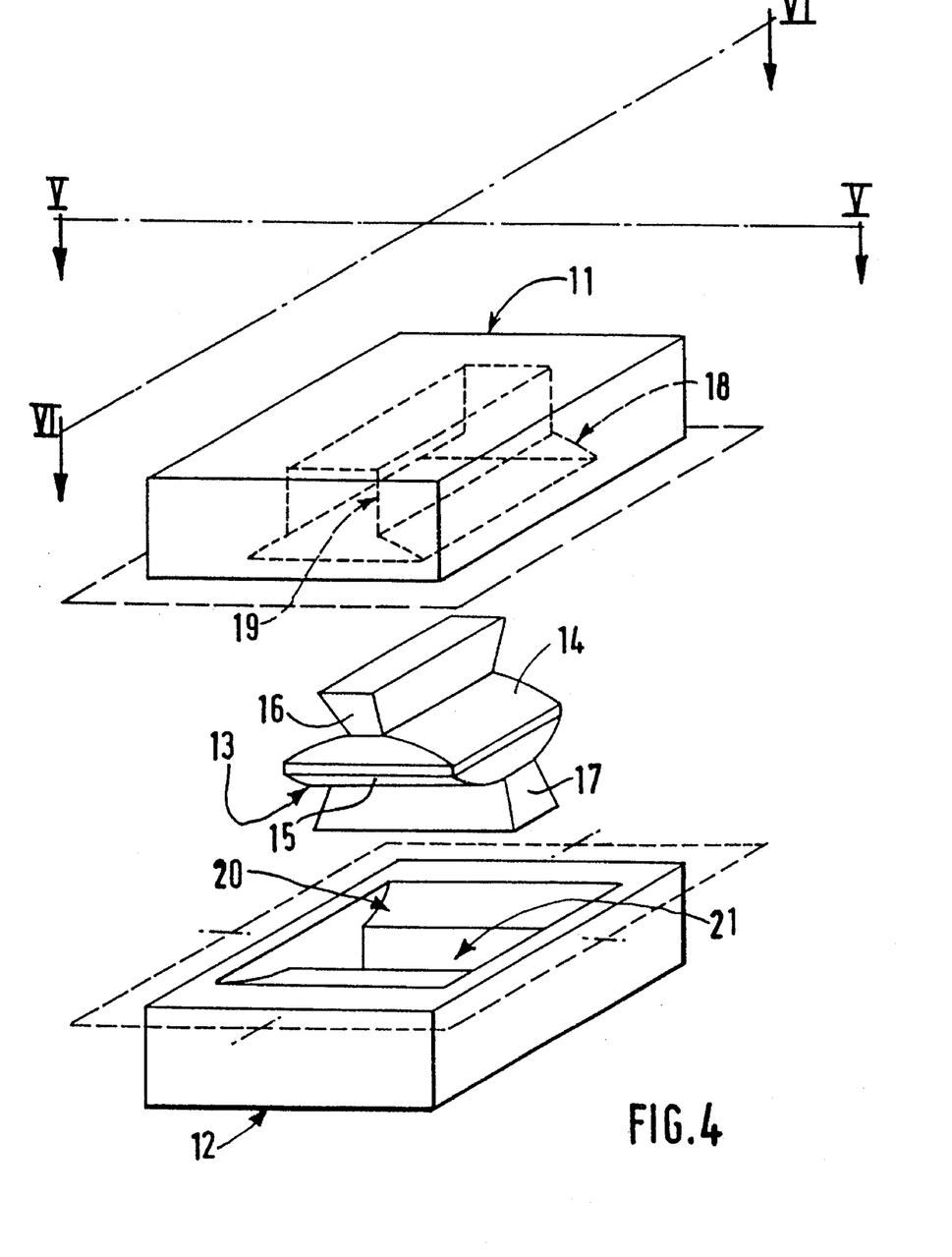
FIG. 4 is a diagrammatic perspective view of another embodiment of the device according to the invention.
Figure 5:
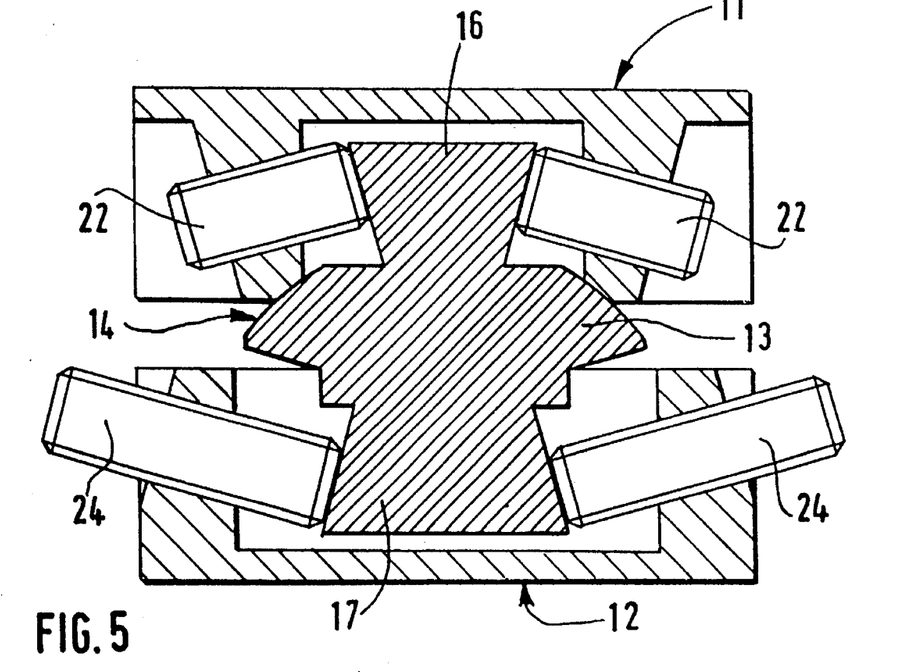
FIGS. 5 and 6 are sectional views along the lines V—V and VI—VI in FIG. 4.
Figure 6:
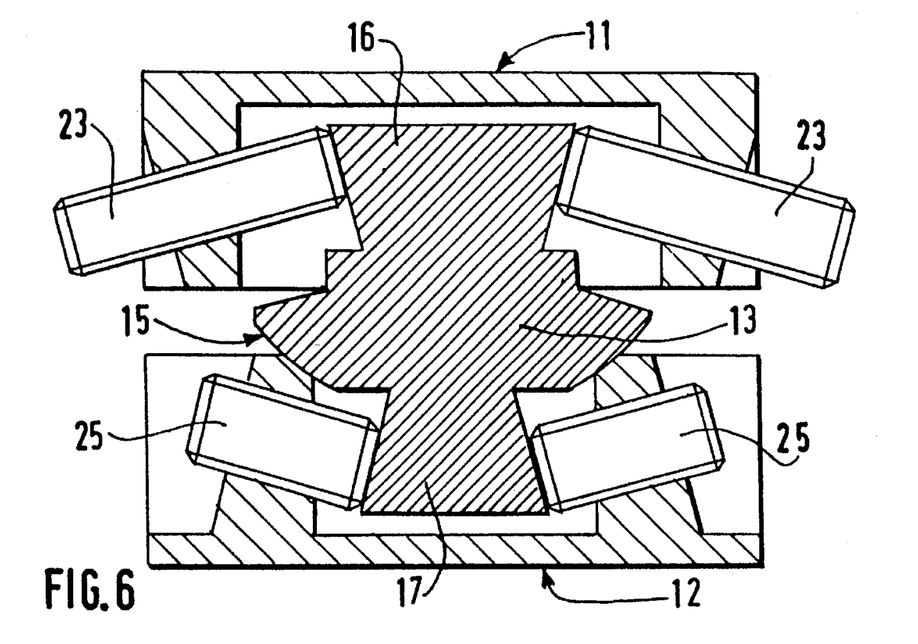

FIGS. 4 to 6 represent a preferred form of implementation of the invention.

As can be seen, the device comprises two plates, 11 and 12 respectively, which are capable of being made integral, respectively, with two parts of a prosthesis, by conventional means (not shown) and an intermediate element 13 which is capable of being made integral, in a plurality of positions, with each of the elements 11 and 12.

The element 13 consists of a nut comprising two cylindrical portions 14 and 15, having perpendicular axes, from each of which there projects, respectively, two portions 16 and 17, in the form of a truncated pyramid with a rectangular base, which adjoin, via their small base, the associated cylindrical portion, with their large base being spaced apart from this cylindrical portion. The large sides of the large bases of the portions 16 and 17 in the form of a truncated pyramid are parallel to the axes of the cylindrical portions 14 and 15.

Female parts hollowed out in the elements 11 and 12 are intended to receive, respectively, on the one hand, the male portions 14 and 16 of the element 13, and on the other hand, the male portions 15 and 17 of this element.

The female part hollowed out in the element 11 comprises a cylindrical portion 18, of a form complementary to that of the part 14, and a groove 19, having a substantially parallelepipedal section, directed parallel to the axis of the cylindrical part 14. The transverse dimension of this groove 19, that is to say the dimension perpendicular to the direction of the axis of the cylindrical part 14, is greater than the corresponding dimension of the part 16 which it is intended to receive. Similarly, the longitudinal dimension of the groove 19, that is to say the dimension parallel to the axis of the cylindrical portion 14, is greater than the corresponding dimension of the part 16.

It is thus possible, on the one hand, to pivot the elements 11 and 13 with respect to one another about the axes of the cylindrical portions 14 and 18 in order to adjust their relative angular position, and, on the other hand, to slide the elements 11 and 13 with respect to one another, by longitudinal displacement of the portion 16 in the groove 19, in order to adjust their respective positions in translation.

In an analogous manner, the female part hollowed out in the element 12 comprises a cylindrical portion 20, of a form complementary to that of the part 15, and a groove 21, having a substantially parallelepipedal section, directed parallel to the axis of the cylindrical part 15. The groove 21 has a length and a width which are greater than the corresponding dimensions of the portion 17, which makes it possible to pivot the cylindrical portions 15 and 20 with respect to one another and to adjust the position of the parts 17 and 21 by translation.

A double adjustment of position is thus possible, in a particularly simple manner, at the level of each of the plates 11 and 12, thus making it possible to adjust the relative positions, both angular and in translation, of the prosthesis parts integral with the plates 11 and 12.

Once this adjustment has been carried out, it will suffice to lock the elements 11 and 13 on the one hand, and 12 and 13 on the other hand, in their relative position in order to retain the position adopted for the prosthesis element. To this end, threaded recesses will be formed transversely in the parts 11 and 12, and screws 22 and 23 on the one hand, and 24 and 25 on the other hand, which are screwed into these recesses, will come into abutment, respectively, against the lateral flanks of the parts 16 and 17 in the form of a truncated pyramid.

It will be noted that the device which has just been described is of great simplicity.

Figure 7:
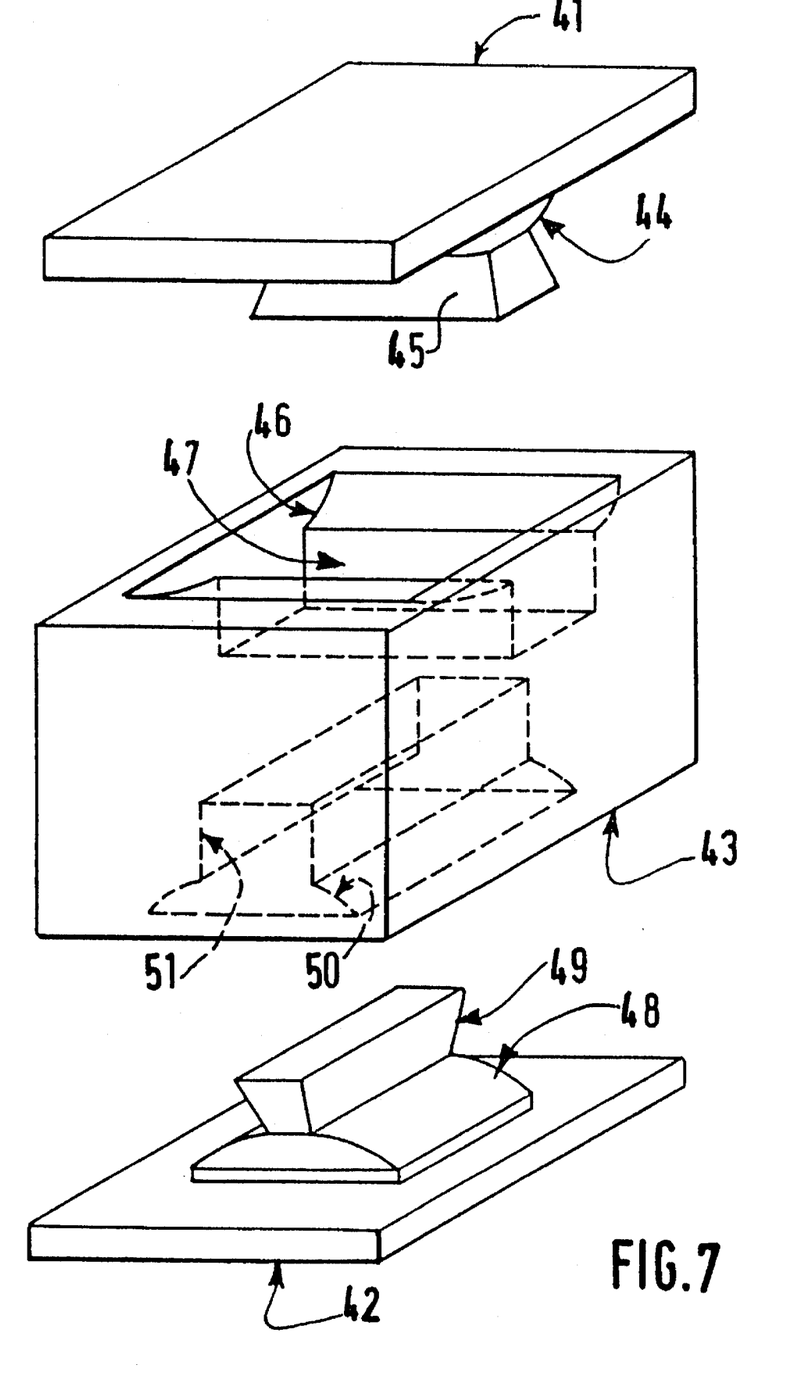
FIGS. 7 and 8 are diagrammatic perspective views of two other forms of implementation of the invention.

Alternatively, as represented in FIG. 7, the male parts can be supported by the elements 41 and 42 which are intended to be made integral with the parts of the prosthesis, and the female parts can be formed in the intermediate element 43.

The male part of the element 41 comprises a cylindrical portion 44 from which there projects a portion 45 in the form of a truncated pyramid, the large base of which is remote from the portion 44. This portion 44 will cooperate with a female portion 46 of complementary profile in the element 43, while the portion 45 is housed in a groove 47 of this element 43, the flanks of which are substantially parallel to the axis of the cylindrical part 44. The transverse and longitudinal dimensions of the groove 47 are greater than the corresponding dimensions of the portion 45, in such a way as to permit a pivoting of the portion 44 with respect to the portion 46 and a sliding of the portion 45 with respect to the groove 47.

In an analogous manner, the element 42 comprises a male cylindrical portion 48, from which there projects a portion 49 in the form of a truncated pyramid. The axis of the portion 49 is perpendicular to that of the portion 44. The portion 48 will be housed in a female portion 50 of complementary profile in the element 43, while the portion 49 will be housed in a groove 51, the flanks of which are parallel to the axis of the part 48, and the longitudinal and transverse dimensions of which are greater than those of the part 49, in such a way as to give the latter a double freedom of movement, permitting a rotation of the portion 48 with respect to the portion 50 and a translation of the portion 49 with respect to the portion 51.

Figure 8:
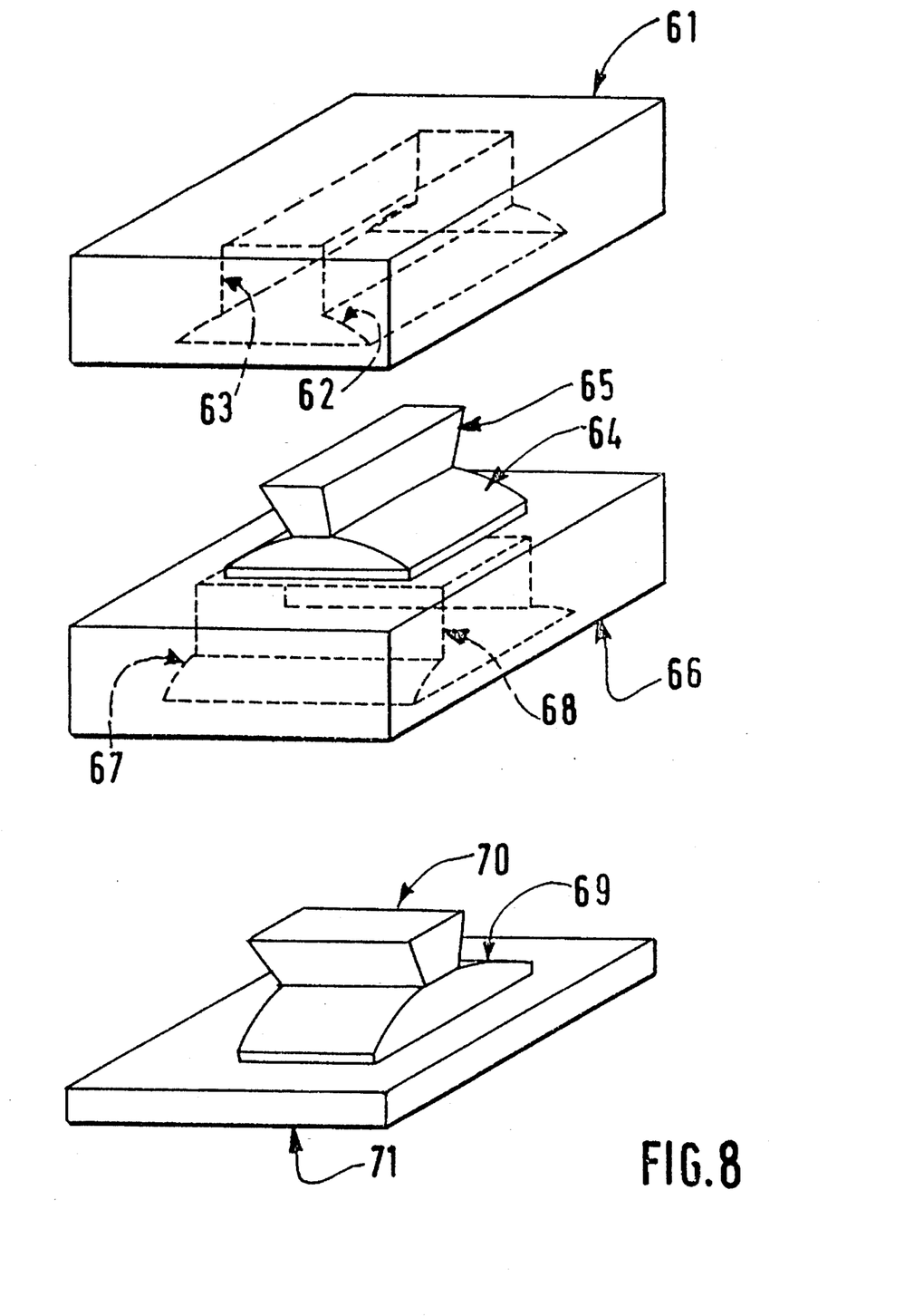

Finally, as represented in FIG. 8, one of the elements intended to be made integral with the parts of the prosthesis, for example the element 61, can comprise a female cylindrical part 62 and a groove 63 with flanks parallel to the axis of the portion 62, these being intended to receive, respectively, a male cylindrical part 64 and a part in the form of a truncated pyramid 65 of the intermediate element 66, while, conversely, a female cylindrical part 67, having an axis perpendicular to that of the part 64, and a groove 68 of the intermediate element 66, with flanks which are substantially parallel to the axis of the cylindrical part 67, will receive, respectively, a male cylindrical part 69, of complementary profile, and a part 70 in the form of a truncated pyramid, projecting with respect to a second element 71 which is intended to be made integral with one of the parts of the prosthesis. As before, the grooves 63 and 68 will have transverse and longitudinal dimensions greater than those of the corresponding parts 65 and 70.

In these three embodiments, the adjustment of the position of the three components of the device is particularly easy to carry out, but it is still possible to provide a further degree of adjustment of the position of these components, in rotation about an axis perpendicular to the axis of pivoting of the cylindrical surfaces.

Figure 9:
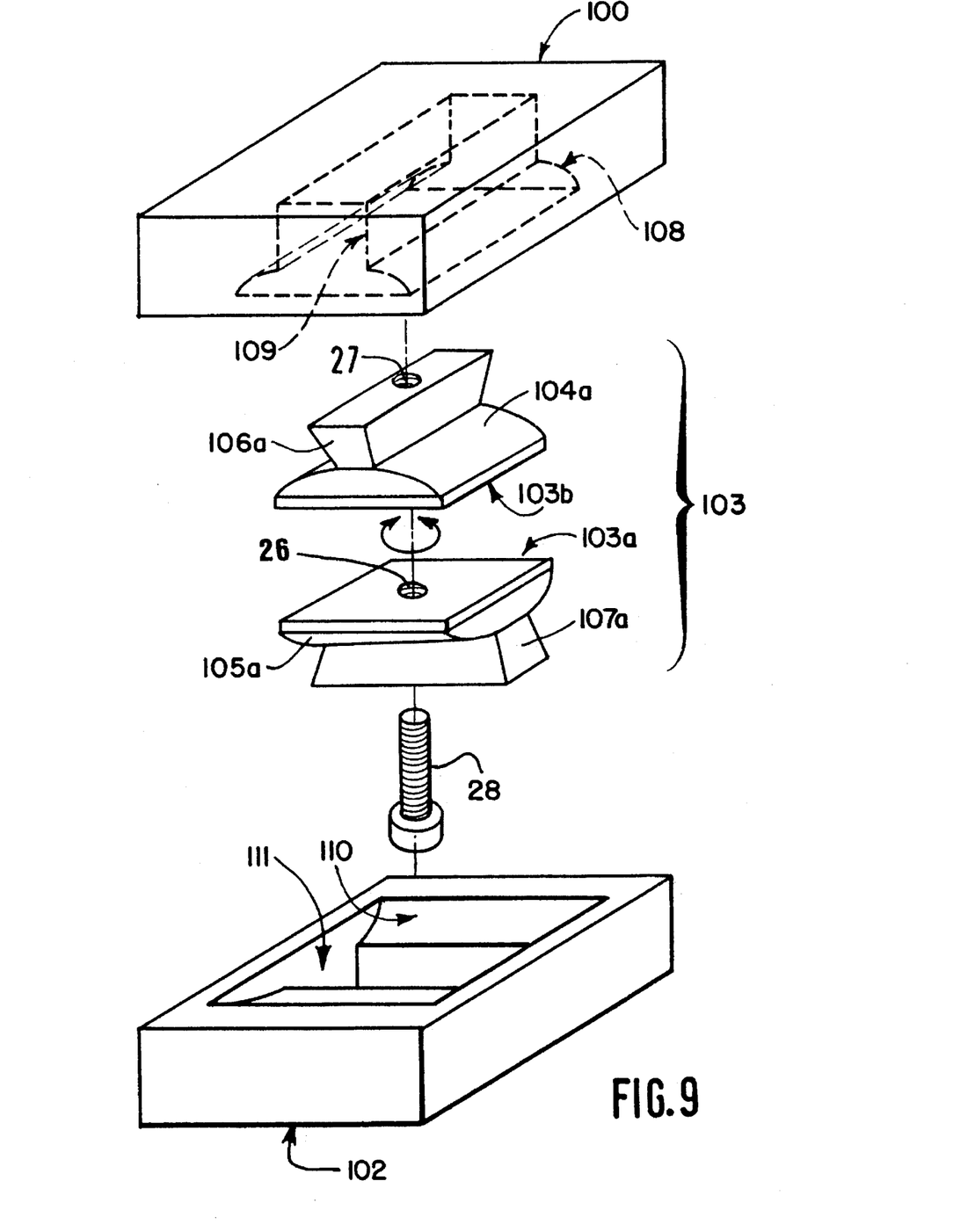
FIGS. 9, 10 and 11 are diagrammatic perspective views of alternative embodiments of the devices in FIGS. 4, 7 and 1, respectively.

This is what is illustrated by FIG. 9 which is to be compared with FIG. 4 described hereinabove and on which the members already described in relation to this FIG. 4 are designated by the same references allocated the prefix "100".

In this embodiment, the intermediate piece 103 consists of two parts 103a and 103b in contact via a flat surface parallel to the axis of the cylindrical surfaces, assembled together with the aid of a screw 28 perpendicular to this axis and screwed into threaded recesses 26 and 27, respectively, in the part 103a and the part 103b.

It is thus possible to adjust, as desired, the angular position of the parts 103a and 103b with respect to one another and then to lock them in position with the aid of the screw 28.

In an analogous manner, the intermediate piece 43 in FIG. 7 could be divided into two parts in mutual contact via a flat surface parallel to the axis of pivoting of the cylindrical parts and assembled with the aid of a screw perpendicular to this axis. Alternatively, at least one of the pieces 32 or 34 in this same FIG. 7 could be divided into two parts which are in mutual contact via a flat surface parallel to the axis of pivoting of the cylindrical surfaces and joined via a screw perpendicular to this axis.

Figure 10:
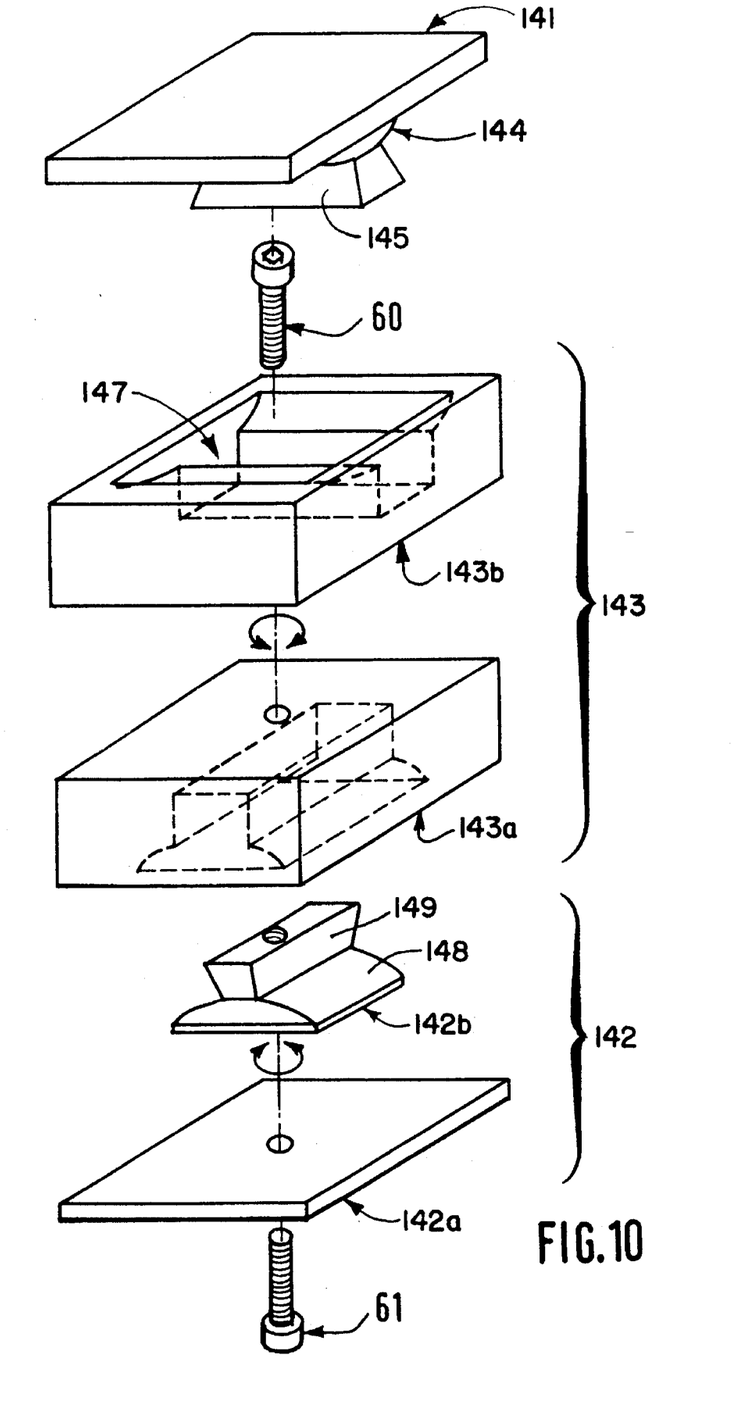

Thus, by way of example, FIG. 10, in which the members already described in relation to FIG. 7 are designated by the same references allocated the prefix "100", represents a device in which the part 143 consists of two parts 143a, 143b, each comprising a female recess, in mutual contact via a flat surface parallel to the axis of the cylindrical surfaces and assembled in a position adjustable in rotation by a screw 60 perpendicular to this axis, while the part 142 is divided into two parts, a plate 142a and a male nut 142b, in mutual contact via a flat surface parallel to the axis of the cylindrical surfaces, and assembled in a position adjustable in rotation by a screw 61.

The additional possibilities of positional adjustment by pivoting one piece with respect to the other are not limited to pieces having a cylindrical surface of corresponding profile.

Figure 11:
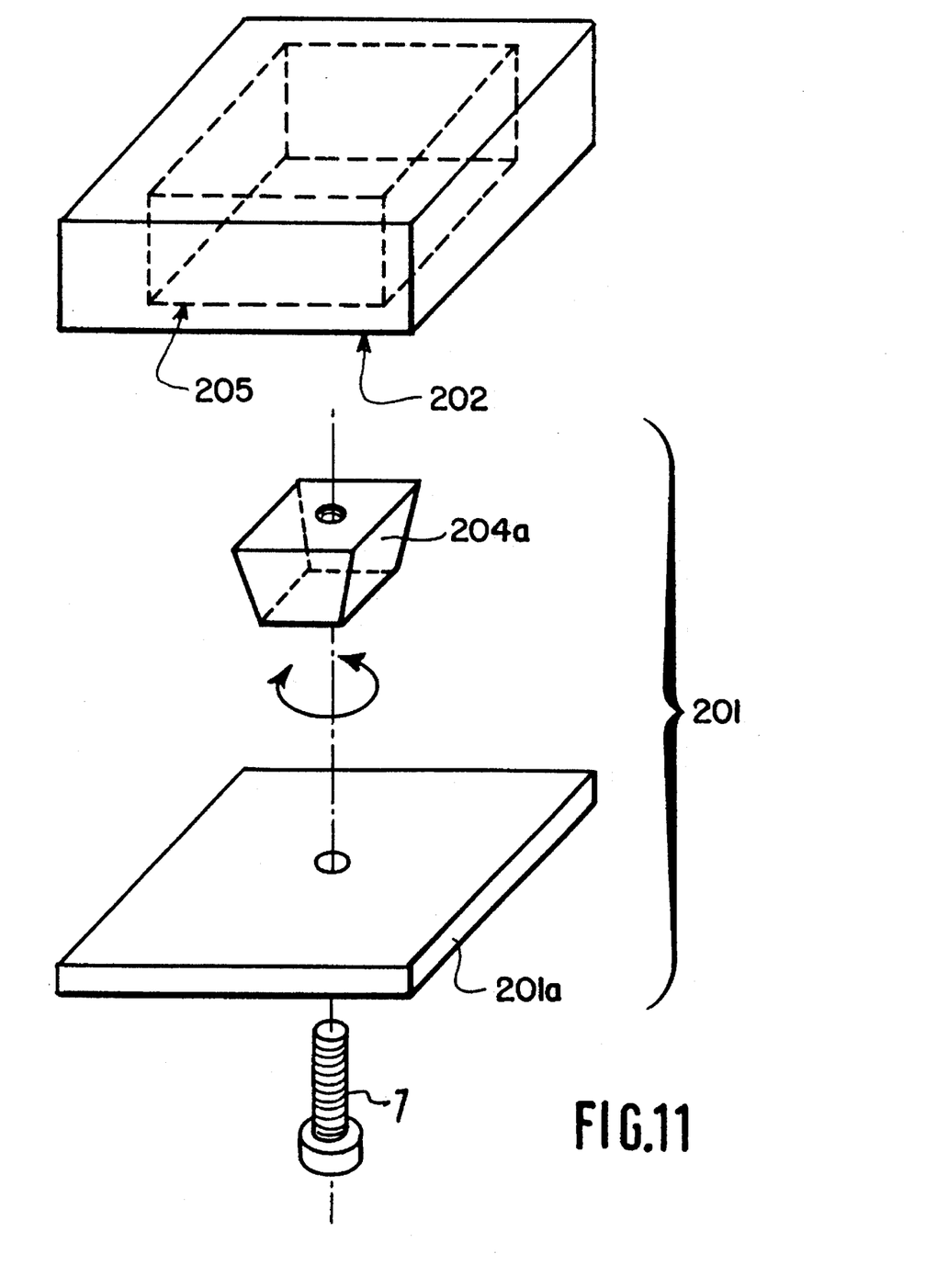

Thus, for example, in the embodiment in FIG. 11, in which the members already described in relation to FIG. 1 are designated using the same references allocated the prefix "200", the male piece 201 consists of two parts, a plate 201a, on which the female part 202 bears, and a male part 204a, the parts 1'a and 204a being in mutual contact via a flat surface and being assembled via a screw 7 perpendicular to this surface. The recess 205 could of course have a profile other than the parallelepipedal profile represented in this figure.

We claim:

1. A system for assembling two components of a prosthesis in a plurality of adjustable positions, said system comprising a projecting part (4) integral with a first one (1) of said components engaged in a rectangular recess forming a hollow part (5) of a second of said components of the prosthesis, said rectangular recess being defined by orthogonal edges, the hollow part (5) having a flat surface extending about the recess and bearing against a flat surface (3) on said first one of said components, said flat surfaces being slidable relative to each other, screws (6) engaged in threaded orthogonally transverse recesses of the hollow part, said screws coming into abutment against orthogonally lateral flanks of the projecting part (4) for locking the projecting part in position relative to the hollow part, each of said flanks having a surface defining a length, the orthogonal edges of the recess forming the hollow part forming a bearing structure, said screws facilitating sliding movement in a rectilinear orientation in at least one direction along substantially the entire length of said lateral flanks, while said projecting part is spaced in any position thereof from a base surface of the recess forming the hollow part.

2. A system according to claim 1, wherein the lateral flanks of the projecting part (4) are inclined relative to the flat surface on said first one of said components.

3. A system according to claim 2, wherein the projecting part (4) has the form of an inverted truncated pyramid having a larger base remote from the flat part on said first one of said components.

* * * * *